(12) United States Patent
Christensen

(10) Patent No.: US 6,241,776 B1
(45) Date of Patent: Jun. 5, 2001

(54) PROSTHETIC FOOT WITH REINFORCING MEMBER

(75) Inventor: Roland J. Christensen, Fayette, UT (US)

(73) Assignee: Roland Christensen, Fayette, UT (US)

(*) Notice: Subject to any disclaimer, the term of this patent is extended or adjusted under 35 U.S.C. 154(b) by 0 days.

(21) Appl. No.: 09/348,431

(22) Filed: Jul. 7, 1999

Related U.S. Application Data (63) Continuation-in-part of application No. 08/906,287, filed on Aug. 4, 1997, now Pat. No. 5,944,760.

(51) Int. Cl.[7] .......................................................... A61F 2/66
(52) U.S. Cl. .................................. 623/52; 623/55; 623/56
(58) Field of Search .......................................... 623/50–56

(56) References Cited

U.S. PATENT DOCUMENTS

| | | |
|---|---|---|
| 2,036,830 | 4/1936 | Rowley . |
| 2,453,969 | 11/1948 | Carter . |
| 2,470,480 | 5/1949 | Fogg . |
| 2,640,200 | 6/1953 | Wisbrun . |
| 3,551,914 | 1/1971 | Woodall . |
| 4,547,913 | 10/1985 | Phillips . |
| 4,721,510 | 1/1988 | Cooper et al. . |
| 5,019,109 | 5/1991 | Voisin . |
| 5,037,444 | 8/1991 | Phillips . |
| 5,112,356 | 5/1992 | Harris et al. . |
| 5,116,384 | 5/1992 | Wilson et al. . |
| 5,181,932 | 1/1993 | Phillips . |
| 5,290,319 | 3/1994 | Phillips . |
| 5,387,246 | 2/1995 | Phillips . |
| 5,507,838 | 4/1996 | Chen . |
| 5,514,185 | 5/1996 | Phillips . |
| 5,653,767 | 8/1997 | Allen et al. . |

FOREIGN PATENT DOCUMENTS

| | | |
|---|---|---|
| 295807 | 12/1916 | (DE) . |
| 560606 | 7/1977 | (SU) . |

*Primary Examiner*—David H. Willse
(74) *Attorney, Agent, or Firm*—Thorpe North & Western, LLP (57) ABSTRACT

A prosthetic foot has a forefoot reinforcement member extending from an attachment section, through a curvilinear spring and arch section, to a toe end. A forefoot reinforcement member extends from the arch section above the forefoot member to a free end proximal the attachment section, and within an extreme range of movement of the forefoot member. A heel member may extend from the arch section to a heel end. A heel reinforcement member may extend from the arch section under the forefoot member to a free end proximal the attachment section, and within an extreme range of movement of the forefoot member. A secondary forefoot reinforcement member may extend from the arch section to a free end proximal the toe end.

27 Claims, 4 Drawing Sheets

PROSTHETIC FOOT WITH REINFORCING MEMBER

This application is a continuation-in-part of U.S. patent application Ser. No. 08/906,287, filed Aug. 4, 1997, now U.S. Pat. No. 5,944,760.

BACKGROUND OF THE INVENTION

1. Field of the Invention

The present invention relates to a resilient prosthetic foot that has a reinforcement member to provide reinforcement. More particularly, the present invention relates to a prosthetic foot having at least a resilient forefoot member, and at least one resilient reinforcement member that is engaged after the forefoot or heel members move from a normal range of movement to an extreme range.

2. Prior Art

Many individuals have lost a limb for various reasons including war, accident, or disease.

In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward.

Examples of such energy storing, spring-like feet having a forefoot member and a heel member include U.S. Pat. Nos. 5,037,444 and 4,547,913. U.S. Pat. No. 5,037,444 issued Aug. 6, 1991 to Phillips discloses a prosthetic foot having a forefoot portion and a heel portion. The forefoot portion has an attachment section, a curvilinear spring section, an arch section, and a toe section formed integrally with one another. The heel portion is removably attached to the forefoot portion at the intersection of the arch and toe sections by a bolt and nut. An elastomeric wedge is inserted between the forefoot portion and the heel portion. U.S. Pat. No 4,547,913 issued Oct. 22, 1985 to Phillips discloses a prosthetic foot having a forefoot portion and a heel portion. The forefoot portion and the heel portion are bound together with a "resin impregnated filament binding" by winding the filament around the members.

The stiffness of prosthetic feet typically vary according to the intended use. Feet intended for everyday use typically require a soft feel, and thus incorporate a loose spring. Feet intended for athletic use typically require strength, and thus incorporate a stiff spring. Although different prosthetic feet may be changed to suit the particular activity, such switching is inconvenient and at times it is impossible, such as a sudden need to run to catch, or avoid being hit by a bus. Feet designed for particular purposes are typically unsuited for other purposes. Stiff, athletic feet are too hard for everyday use, and loose, everyday feet are too fragile for athletic use. Multiple-use feet have been designed which are capable of many different uses, but without being particularly well suited for any use.

In addition, the performance of these energy storing feet has been altered in various ways, such as by using multiple springs in various configurations, using bladders or resilient materials disposed between various elements, and using multiple springs that deflect at different intervals of foot deflection to add resistance.

U.S. Pat. No. 5,290,319 issued Mar. 1, 1994 to Phillips discloses a prosthetic foot having a forefoot portion, a heel portion, and an auxiliary member disposed above the forefoot portion. A bladder is disposed between the auxiliary member and the forefoot portion. The pressure in the bladder is varied to adjust the performance of the foot. In this configuration, the auxiliary member is a structural member against which the bladder is compressed.

U.S. Pat. No. 5,387,246 issued Feb. 7, 1995 to Phillips discloses a prosthetic foot having a forefoot portion, a sole member, and an auxiliary or secondary stiffness member disposed above the forefoot portion. The secondary member adds stiffness to the foot when the foot is deflected sufficiently forward such as to engage the secondary member.

U.S. Pat. No. 4,721,510 issued Jan. 26, 1988 to Cooper et al. discloses a prosthetic foot having a relatively flexible primary foot member and a relatively stiff secondary foot member disposed above the primary foot member such that the spring force of the foot is increased as the primary foot member deflects to the secondary foot member.

It is desirable to further improve prosthetic feet to better simulate real feet, and improve the performance and response characteristics of prosthetic feet. Therefore, it would be advantageous to develop a prosthetic foot capable of more naturally simulating a real foot. It would also be advantageous to develop a prosthetic foot having a reinforcement member. In addition, it would be advantageous to develop a prosthetic foot having various degrees of stiffness.

OBJECTS AND SUMMARY OF THE INVENTION

It is an object of the present invention to provide a prosthetic foot capable of better simulating a real foot.

It is another object of the present invention to provide a prosthetic foot capable of various different stiffnesses through a range of motion of the foot.

It is yet another object of the present invention to provide a prosthetic foot with a reinforcement member to reinforce the forefoot, heel, or both.

These and other objects and advantages of the present invention are realized in a prosthetic foot having a resilient forefoot member and a resilient forefoot reinforcement member. The forefoot member has a base end coupled proximal an attachment location, and extends forward to a toe end at a toe location. In addition, the forefoot member defines an arch section between the base end and the toe end. The forefoot member moves through a range of motion with multiple stages of advancement, including at least a normal range and an extreme range. The resilient forefoot member has a resistance response to an applied force.

The forefoot reinforcement member has a base section coupled to the forefoot member at the arch section, and extends to a free end at a location between the arch section and the attachment location. The free end is spaced from the forefoot member and is disposed within the extreme range of motion of the forefoot member. The reinforcement member itself has a range of motion within the extreme range of motion of the forefoot member. Thus, the forefoot reinforcement member influences the range of motion and resistance response of the forefoot member.

In accordance with one aspect of the present invention, a flexible restraint may be coupled to and between the free end of the forefoot reinforcement member and the forefoot member. The restraint allows the forefoot member to move towards the forefoot reinforcement member, but couples the forefoot member to the forefoot reinforcement member in movement away from the forefoot reinforcement member.

In accordance with another aspect of the present invention, a resilient heel member has a-base end coupled to the resilient forefoot member, and extends rearward to a heel end at a heel location. Like the forefoot member, the heel member has a range of motion including a normal range and an extreme range, and has a resistance response to an applied force.

In accordance with another aspect of the present invention, a heel reinforcement member has a base section coupled to the forefoot member at the arch section, and extends under the forefoot member to a free end proximal the attachment location. The free section is disposed within the extreme range of motion of the forefoot member. Like the forefoot reinforcement member, the heel reinforcement member has a range of motion within the extreme range of motion of the forefoot member, and thus, the heel reinforcement member influences the range of motion and resistance response of the forefoot member and the heel member.

In accordance with another aspect of the present invention, a flexible cushion is disposed between the free end of the forefoot reinforcement member and the forefoot member. Likewise, such a cushion may be disposed between the heel reinforcement member and the forefoot member. In addition, an air bag containing air may be disposed between the members.

In accordance with another aspect of the present invention, a secondary forefoot reinforcement member has a base section coupled to the forefoot member at the arch section, and extending to a free end proximal the toe location. The free end is spaced above the toe end of the forefoot member, and is disposed within the extreme range of motion of the forefoot member, or toe end. The secondary forefoot reinforcement member has a range of motion within the extreme range of motion of the forefoot member, or toe end, and thus, influences the range of motion and resistance response of the forefoot member.

In accordance with another aspect of the present invention, the heel reinforcement member forms an arcuate section which extends near the heel location, and within the extreme range of motion of the heel member.

In accordance with another aspect of the present invention, flexible and resilient wedge members are disposed between the members to strengthen and/or stiffen various regions of the foot. For example, wedge members may be positioned between the forefoot member and the forefoot reinforcement member at a location proximal to the attachment. Similarly, a wedge member may be positioned between the forefoot and heel members near the attachment.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Figure 1:
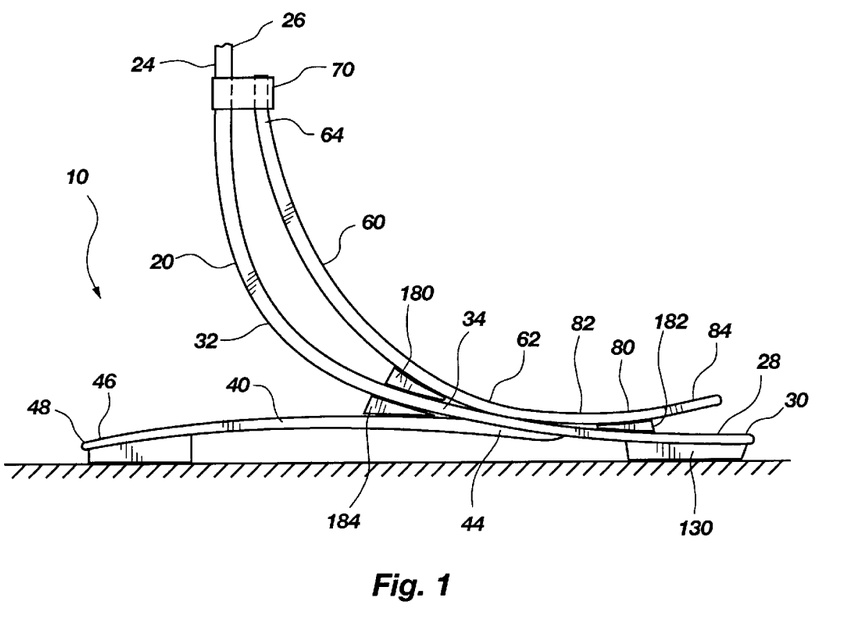
FIG. 1 is a side elevational view of a preferred embodiment of a prosthetic foot of the present invention.

Reference will now be made to the drawings in which the various elements of the present invention will be given numerical designations and in which the invention will be discussed so as to enable one skilled in the art to make and use the invention. As illustrated in FIG. 1, a preferred embodiment of a prosthetic foot 10 of the present invention is shown. The prosthetic foot 10 has a resilient forefoot member 20. The forefoot member 20 has a base end 24 coupled near an attachment location 26. The attachment location 26 is near a stump of an amputee, and the base end 24 of the forefoot member 20 attaches to a socket (not shown) for receiving the stump of the amputee. The socket is configured for the specific needs of the amputee but typically has a portion adapted for standard attachment. The base end 24 of the forefoot member 20 may be attached to the socket by any means such as by nut and bolt.

The forefoot member 20 extends forward from the base end 24 to a toe end 28 at a general toe location 30. The toe location 30 is a region near the forward end of the foot where toes of a natural foot would be located. In addition, the forefoot member 20 forms a vertically oriented arc extending between the base end 24 at the attachment location 26, and the toe end 28 at the toe location 30. The forefoot member 20 has a curvilinear spring portion 32 extending from the base end 24, and an arch portion 34 extending from the spring portion 32 to the toe end 28.

The forefoot member 20 is preferably made of a resilient material. As the user steps, or pivots forward, on the prosthetic foot 10, the forefoot member 20 deflects. Because the forefoot member 20 is made of a resilient material, the forefoot member 20 acts as a spring, and stores the energy to be released as the user moves forward.

The forefoot member 20 has a range of motion with multiple stages of advancement. The member engages a surface, such as the ground, either directly or through a shoe. As the user steps, or pivots forward, on the prosthetic foot 10, an applied force, such as the user's weight, causes the member to deflect through the range of motion. The range of motion includes at least a normal range and an extreme range. The forefoot member 20 moves through the normal range during normal activity, and through the normal range and into the extreme range during extreme activity. The normal activity includes activities such as walking and standing. The extreme activity includes activities which deflect the forefoot member beyond the normal range and deflection, such as when running and jumping.

The forefoot member 20 also has a resistance response to an applied force. The resistance response is the stiffness or spring force exerted by the member in response to the applied force. The applied force includes the static weight of the user, and dynamic impact forces exerted on the foot during use.

The prosthetic foot 10 preferably has a resilient heel member 40. The heel member 40 has a base end 44 coupled to the forefoot member 20. The base end 44 of the heel member 40 preferably is coupled to the forefoot member 20 at the arch portion 34. The heel member 40 extends rearward from the base end 44 to a heel end 46 at a general heel location 48. The heel location 48 is a region near the rearward end of the foot where the heel of a natural foot would be located. The heel member 40 preferably forms an arc extending between the base end 44 and the heel end 46 at the heel location 48. It is of course understood that the heel members may be coupled to the forefoot member at any appropriate location, including the attachment location.

Figure 5:
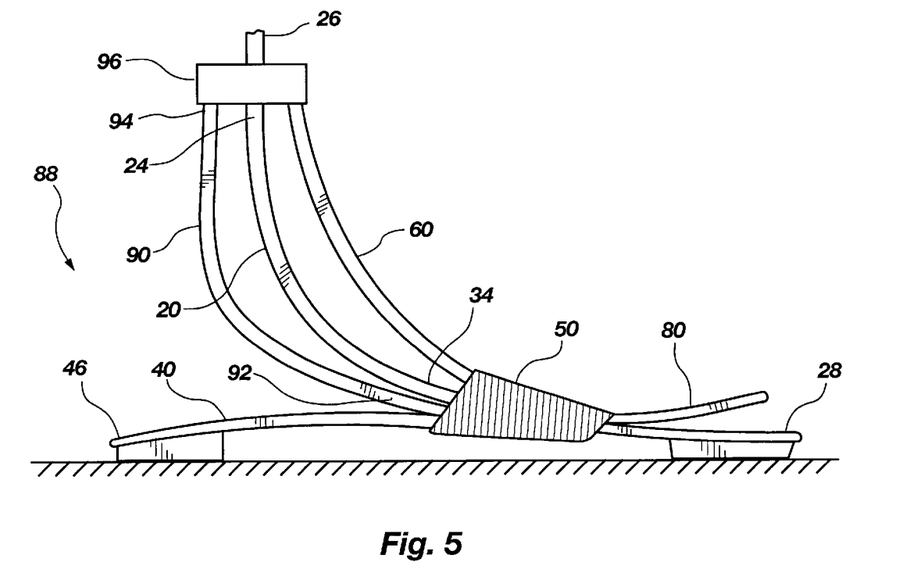
FIG. 5 is a side elevational view of an alternative embodiment of a prosthetic foot of the present invention.

The heel member 40 may be attached to the forefoot member 20 by wrapping the base end 44 of the heel member 40 and the arch portion 34 of the forefoot member 20 with a resin impregnated fiber 50, as shown in FIG. 5. Alternatively, any appropriate means may be used including bolting or even forming the heel members integrally with the forefoot members.

The heel member 40 is also made of a resilient material. As the user steps on the prosthetic foot 10, the heel member 40 deflects. Because the heel member 40 is made of a resilient material, it acts as a spring and cushions the force of the foot 10 as it contacts the ground, and stores energy.

The heel member 40 also has a range of motion with multiple stages of advancement. The members engage a surface, such as the ground, either directly or through a shoe. As the user steps on the prosthetic foot 10, an applied force, such as the user's weight, causes the member to deflect through the range of motion. The range of motion includes at least a normal range and an extreme range. The heel member 40 moves through the normal range during normal activity, and through the normal range and into the extreme range during extreme activity. The heel member 40 also has a resistance response to an applied force.

The prosthetic foot 10 advantageously has at least one resilient reinforcement member, such as a forefoot reinforcement member, or heel reinforcement member. The reinforcement member has a base section coupled to the forefoot member and extends to a free section. The free section operates within the extreme range of motion of the forefoot member, and/or the heel member, and may be freely moveable with respect to the members. The reinforcement member influences the range of motion and resistance response of the forefoot member and/or heel member. In the preferred embodiment, the foot 10 has a forefoot reinforcement member 60. The forefoot reinforcement member 60 has a base section 62 coupled to the upper or top side of the forefoot member 20. The base section 62 is preferably coupled to the arch portion 34 of the forefoot member 20. The forefoot reinforcement member 60 extends above the forefoot member 20 to a free section 64 at a location between the arch section 34 and the attachment location 26, and preferably proximal to the attachment location 26. The free section 64 of the forefoot reinforcement member 60 is not rigidly attached to the forefoot member 20, but is moveable with respect to the forefoot member 20. The free section 64 may be non-rigidly coupled to the forefoot member 20 as discussed below. The free section 64 operates within the extreme range of motion of the forefoot member 20.

The prosthetic foot 10 may also have a flexible restraint 70, such as a strap, coupled to and between the free end 64 of the forefoot reinforcement member 60 and the forefoot member 20. The restraint 70 is flexible in the direction of the forefoot member 20 and forefoot reinforcement member 60 towards one another, but substantially non-flexible in the direction of the forefoot member 20 and forefoot reinforcement member 60 away from one another. Thus, restraint 70 allows the forefoot member 20 to move or deflect towards the reinforcement member 60, but couples the reinforcement member 60 to the forefoot member 20 as the forefoot member 20 moves or deflects away from the reinforcement member 60. Therefore, the restraint 70 transfers some of the heel load to the forefoot reinforcement member 60, as discussed more fully below. The restraint 70 may also have some play or slop of predetermined length to allow the reinforcement member 60 to move or deflect away from the forefoot member 20 a predetermined distance before operatively coupling them together. The restraint 70 may be a strap or any other suitable means for coupling the reinforcement member 60 to the forefoot member 20, such as a nylon cord or wire cable. It may also comprise a resilient polymer.

Figure 2:
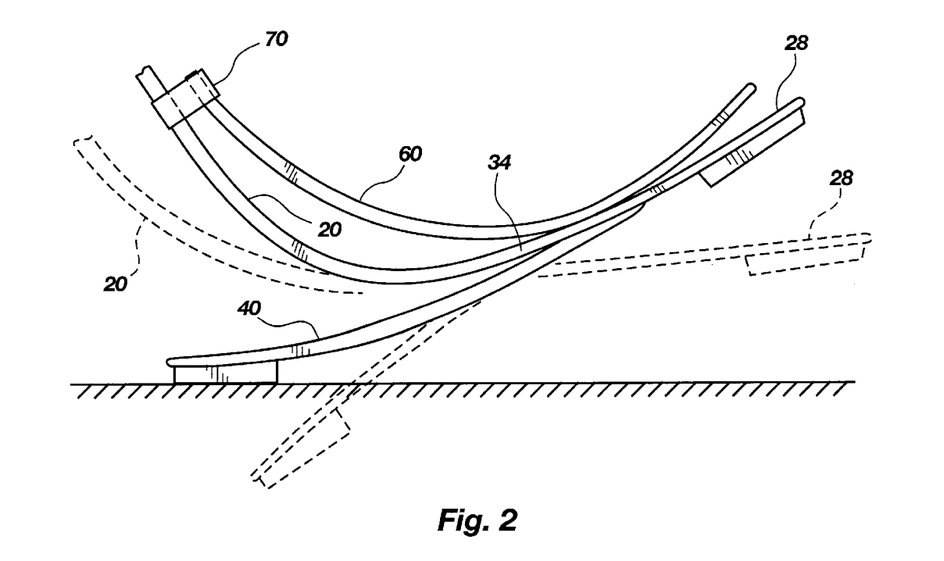
FIGS. 2–4 are schematic views of the operation of the preferred embodiment of the prosthetic foot of the present invention.
Figure 3:
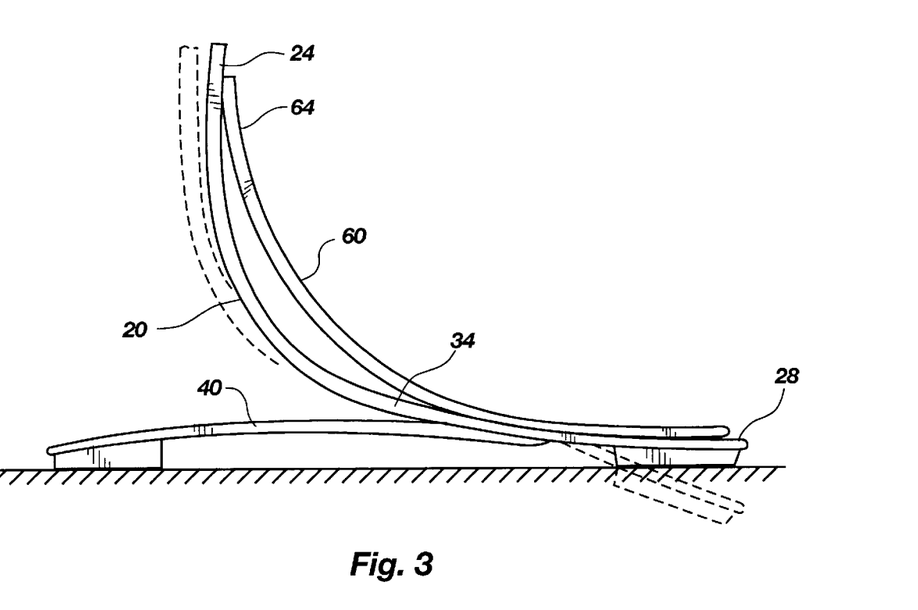
Figure 4:
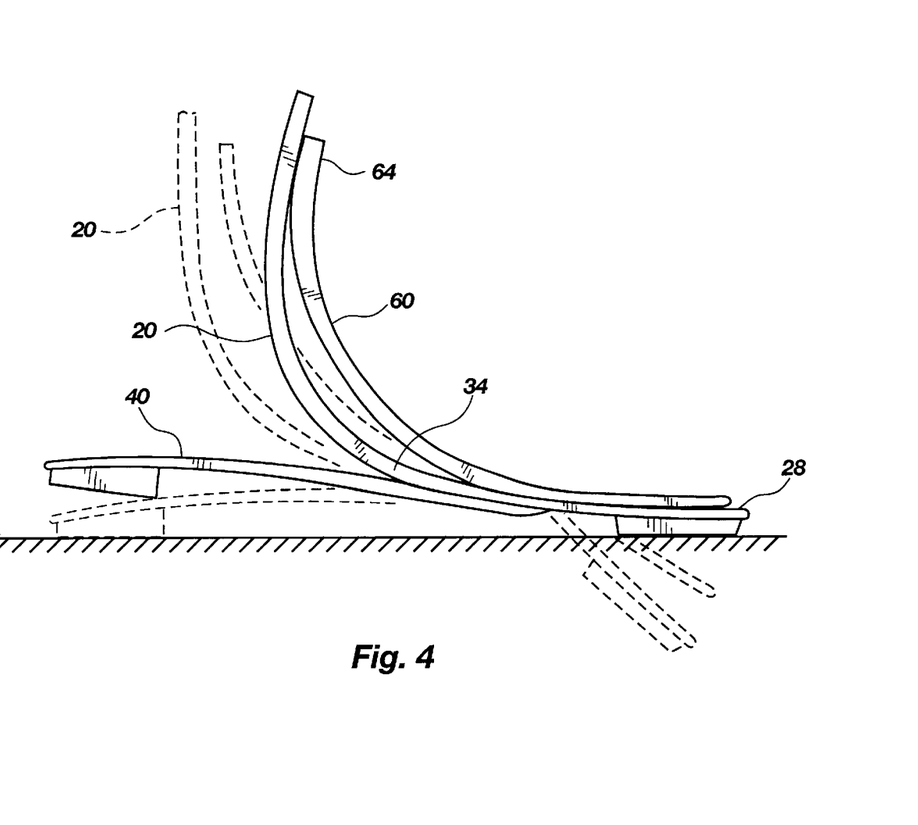

Referring to FIGS. 2–4, the operation of the prosthetic foot 10 of the present invention is demonstrated. Referring to FIG. 2, in normal use, the heel member 40 deflects, or moves, through the normal range of motion as the user steps onto the foot 10. The heel member 40 engages the surface and the applied force of the user's weight causes the heel member 40 to deflect through a range of motion, indicated between the solid and dashed lines of the heel member 40. The heel member 40 is shown in a deflected position in solid lines, and in an initial position in dashed lines which may have only static loads or which may be unstressed or deflected. As the heel member 40 and the forefoot member 20 deflect or bend towards one another under the user's weight, the attachment of the heel member 40 to the forefoot member 20 tends to deflect or flex the forefoot member 20, as indicated by the phantom lines of the toe end 28 and arch portion 34. The restraint 70, however, couples the forefoot reinforcement member 60 to the forefoot member 20 to reinforce the forefoot member 20 and adds additional resistance to movement or deflection of the forefoot member 20. In addition, coupling the reinforcement member 60 to the forefoot member 20 resists flexion or bending of the forefoot member 20, and the arch portion 34.

Referring to FIG. 3, the forefoot member 20 also deflects, or moves, through the normal range of motion as the user pivots forward on the foot 10. The forefoot member 20 engages the surface and the applied force of the user's weight causes the members to deflect through a range of motion, indicated between the solid and dashed lines of the forefoot member 20. The forefoot member 20 is shown in a deflected position in solid lines, and in an initial position in dashed lines which may have only static loads or which may be unstressed or deflected. The normal range of motion is a result of normal activities, such as walking, that exert a normal applied force on the foot.

Referring to FIG. 4, during extreme activities, such as running, a more extreme applied force is exerted on the foot resulting in an extreme range of motion. The greater the force exerted on the foot, the greater the deflection, or movement in the range of motion. In extreme use, the forefoot member 20 engages the free section 64 of the forefoot reinforcement member 60 and they deflect together. During extreme activities, the reinforcement member is advantageously engaged to add stiffness and strength to the foot 10, or the forefoot member 20. Because of the reinforcement member 60, softer or less resistant heel and forefoot members may be used for a softer, more cushioned feel without the fear of failure or need to change prosthetics should the need for greater activity arise.

The present invention provides a significant improvement over prior art prosthetic feet by providing a multipurpose foot, having a reinforcement member to add stiffness during extreme activities while maintaining the softer heel and forefoot members during normal activities.

Referring again to FIG. 1, the prosthetic foot 10 of the present invention preferably and advantageously has a secondary forefoot reinforcement member 80. The secondary forefoot reinforcement member 80 has a base section 82 fixedly coupled to the upper or top side of the forefoot member 20 at the arch portion 34. The secondary forefoot reinforcement member 80 extends above the forefoot member 20 to a free section 84 proximal the toe location 30 and spaced above the toe end 28. The free section 84 of the secondary forefoot reinforcement member 80 is not rigidly attached to the forefoot member 20. The free section 84 operates within the extreme range of motion of the forefoot member 20, or the toe end 28, and has a range of motion within the extreme range of motion of the forefoot member 20, or toe end 28.

Referring again to FIG. 3, the toe end 28 of the forefoot member 20 deflects, or moves, through the normal range of motion as the user pivots forward on the foot 10. Referring again to FIG. 4, in extreme use, the toe end 28 of the forefoot member 20 engages the free section 84 of the secondary forefoot reinforcement member 80 and they deflect together. During extreme activities, the secondary reinforcement member is advantageously engaged to add stiffness and strength to the foot 10, or the toe end 28 of the forefoot member 20, and the arch portion 34.

The primary and secondary forefoot reinforcement members 60 and 80 may be integrally formed, as shown, with the base end 82 of the secondary member 80 being integrally formed with the base end 62 of the primary member 60. Thus, both members 60 and 80 extend from the arch portion 34 in opposite directions. Alternatively, the members 60 and 80 may be separate members.

The configuration of the reinforcement member with respect to the heel and forefoot members may take various forms, examples of which are illustrated and described in the alternative embodiments. Referring to FIG. 5, an alternative embodiment of the prosthetic foot 88 may have a heel reinforcement member 90. The heel reinforcement member 90 has a base section 92 coupled to the lower side or bottom of the forefoot member 20, preferably at the arch portion 34. The heel reinforcement member 90 extends rearward to a free section 94 at a location between the arch portion 34 and the attachment section 26, and preferably proximal to the attachment location 26. The free section 94 is disposed within the extreme range of motion of the forefoot member 20, and may be freely moveable with respect to the forefoot member 20. The heel reinforcement member 90 has a range of motion within the extreme range of motion of the forefoot member 20.

As described above, a flexible restraint 96, such as a strap, may be coupled to and between the free end 94 of the heel reinforcement member 90 and the forefoot member 20. Again, the restraint 96 is flexible in the direction of the forefoot member 20 and heel reinforcement member 90 towards one another, but substantially non-flexible in the direction of the members 20 and 90 away from one another. Thus, the heel reinforcement member 90 allows the forefoot member 20 to move towards the heel reinforcement member 90, but couples the forefoot member 20 to the heel reinforcement member 90 in movement away from the heel reinforcement member 90. Therefore, the restraint 96 transfers some of the load to the heel reinforcement member 90. In addition, the restraint 96 may have a predetermined play or slop to allow movement away from each other. Together, the forefoot and heel reinforcement members 60 and 90 reinforce the forefoot member 20 in the extreme range of movement, but in opposite directions of movement while the forefoot member 20 is in the normal range of movement.

Figure 6:
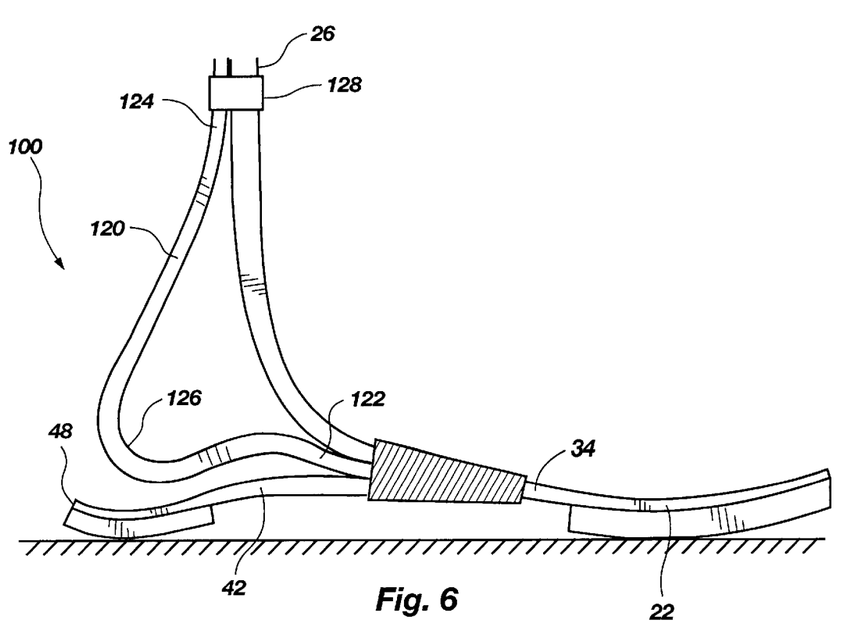
FIG. 6 is a side elevational view of an alternative embodiment of a prosthetic foot of the present invention.

Referring to FIG. 6, an alternative embodiment of the prosthetic foot 100 of the present invention may have only a heel reinforcement member 120. The heel reinforcement member 120 has a base section 122 coupled to the bottom of the forefoot member 20 near the arch location 34. The heel reinforcement member 120 extends to a free section 124 above the arch 34 and preferably near the attachment location 26. The reinforcement member 120 forms an arcuate section 126 that extends near the heel location 48. In this configuration, the reinforcement member 120 reinforces both the heel member 40 and forefoot member 20. The arcuate section 126 is engaged as the heel member moves into the extreme range of motion. A strap 128 couples the free section of the reinforcement member 120 to the forefoot member 20. As the forefoot member 20 moves into the extreme range of motion, the reinforcement member 120 reinforces the forefoot member 20.

Referring again to FIG. 1, cushions 130 may be disposed on the bottoms of the heel and forefoot members 40 and 20 to soften or cushion the contact between the members and the surface.

Figure 7:
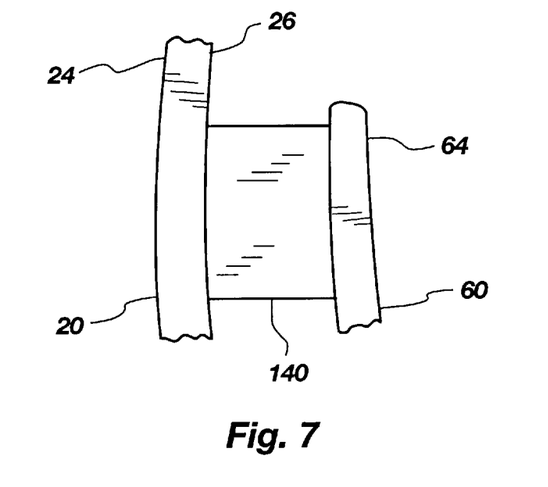
FIG. 7 is a partial side view of the preferred embodiment of the prosthetic foot of the present invention.
Figure 8:
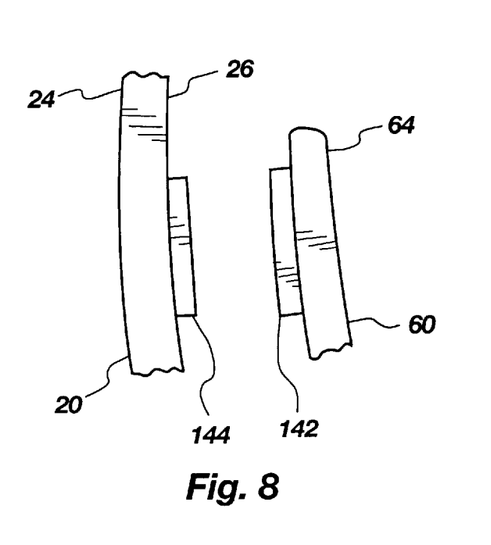
FIG. 8 is a partial side view of an alternative embodiment of the prosthetic foot of the present invention.

Referring to FIG. 7, a flexible cushion 140 may be disposed between the free end 64 of the forefoot reinforcement member 60 and the forefoot member 20 to cushion the contact between the two members 20 and 60. The cushion 140 may be a foam rubber material or the like adhered to one or both surfaces of the members 20 and 60. As shown, the cushion 140 may substantially fill the space or distance between the two members 20 and 60. Alternatively, referring to FIG. 8, the cushion may be comprised of one or more cushions, such as a first cushion 142 attached to the reinforcement member 60, and/or a second cushion 144 attached to the forefoot member 20. The cushions 140, 142 and 144 not only cushion the contact between the two members 20 and 60, but gradually transfer force between the two members 20 and 60, or gradually change the resistance as the forefoot member 20 moves into the extreme range of movement and contacts the reinforcement member 60. Thus, the response of the foot 10 is a soft resistance by the forefoot member 20 and then an abrupt, stiff or hard resistance from both the forefoot and reinforcement members 20 and 60, but a soft response by the forefoot member 20 gradually transitioning through an increasingly hard and stiff resistance as the cushion 140, 142 and/or 144 is increasingly compressed.

Figure 9:
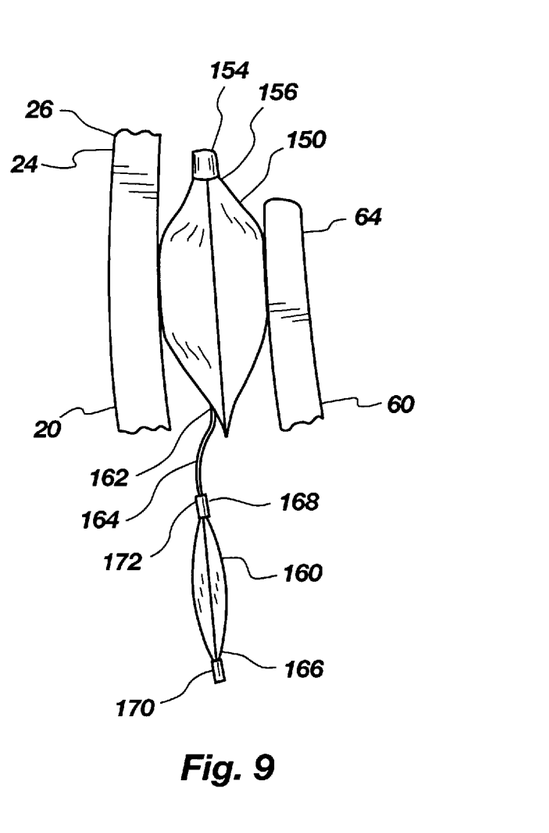
FIG. 9 is a partial side view of an alternative embodiment of the prosthetic foot of the present invention.

Referring to FIG. 9, an air bag or bladder 150 containing air may be disposed between the forefoot member 20 and reinforcement member 60. A valve 154, such as a pin or needle valve, may be coupled to an opening 156 in the bag for releasing, and thus adjusting, the pressure of air in the bag 150. By adjusting the air pressure in the bag 150, the stiffness of the bag 150 is adjusted, and the performance characteristics of the foot 10 are varied. A small air pump 160 may be coupled to an opening 162 in the bag 150 by a tube 164. The pump 160 may be a resilient bladder such that the bladder may be compressed, forcing out air, and released, drawing in air as the resilient bladder returns to its initial shape. The bladder has an air inlet 166 and an air outlet 168, and check valves 170 and 172 coupled to the inlet and outlet 168, respectively, such that air is permitted through the check valve 170 at the inlet 166 and into the bladder as the bladder expands, and out the check valve 172 at the outlet 168 as the bladder is compressed. The pump 160 may be secured to either member 20 or 60 in a convenient location, or may be releaseably secured to the air bag 150.

It is of course understood that the above discussion with respect to the cushion 140 and air bag 150 being disposed between the forefoot member 20 and forefoot reinforcement member 60 is equally applicable to a cushion or air bag being disposed between the forefoot member 20 and the heel reinforcement member 90.

Referring again to FIG. 1, flexible and resilient wedge members may be disposed between the various members to strengthen and/or stiffen the foot. The wedge members may have various different stiffness. For example, a wedge member 180 may be positioned between the forefoot member 20 and the forefoot reinforcement member 60 at a location proximal to the attachment. Another wedge member 182 may be positioned between the forefoot member 20 and the secondary forefoot reinforcement member 80. In addition, a wedge member 184 may be positioned between the forefoot and heel members 20 and 40 proximal to the attachment.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

What is claimed is:

1. A prosthetic foot comprising:
   a resilient forefoot member having a base end coupled proximal an attachment location and extending forward to a toe end at a toe location, the forefoot member defining a curvilinear spring portion located at an ankle location of a natural foot and extending from the base end, and an arch section located at an arch location of a natural foot and extending from the spring portion to the toe end, and having a range of motion with multiple stages of advancement including at least a normal range and an extreme range and having a resistance response to an applied force; and
   a forefoot reinforcement member having a base section coupled to the arch section of the forefoot member and extending to a free end at a location between the arch section and the attachment location and spaced from the forefoot member, the free end being disposed within the extreme range of motion of the forefoot member and having a range of motion within the extreme range of motion of the forefoot member, such that the forefoot reinforcement member influences the range of motion and resistance response of the forefoot member.

2. The prosthetic foot of claim 1, further comprising:
   a flexible restraint coupled to and between the free end of the forefoot reinforcement member and the forefoot member, the restraint being flexible in a direction towards the forefoot reinforcement member to allow the forefoot member to move towards the forefoot reinforcement member, but substantially non-flexible in a direction away from the forefoot reinforcement member to couple the forefoot member to the forefoot reinforcement member in movement away from the forefoot reinforcement member.

3. The prosthetic foot of claim 1, further comprising:
   a resilient heel member having a base end coupled to the resilient forefoot member and extending rearward to a heel end at a heel location, the heel member having a range of motion including a normal range and an extreme range and having a resistance response to an applied force.

4. The prosthetic foot of claim 1, wherein a flexible cushion is disposed between the free end of the forefoot reinforcement member and the forefoot member.

5. The prosthetic foot of claim 1, wherein an air bag containing air is disposed between the free end of the forefoot reinforcement member and the forefoot member.

6. The prosthetic foot of claim 5, wherein the air bag has an opening; and further comprising means for varying the pressure of the air in the air bag coupled to the opening.

7. The prosthetic foot of claim 1, further comprising:
   a secondary forefoot reinforcement member having a base section coupled to the forefoot member at the arch section and extending to a free end proximal the toe location and spaced above the toe end of the forefoot member, the free end of the secondary forefoot reinforcement member being disposed within the extreme range of motion of the forefoot member and having a range of motion within the extreme range of motion of the forefoot member, such that the secondary forefoot reinforcement member influences the range of motion and resistance response of the forefoot member.

8. The prosthetic foot of claim 1, further comprising:
   a heel reinforcement member having a base section coupled to the forefoot member at the arch section and extending under the forefoot member to a free end proximal the attachment location, the free end being disposed within the extreme range of motion of the forefoot member and moveable with respect to the forefoot member, the heel reinforcement member having a range of motion within the extreme range of motion of the forefoot member, such that the heel reinforcement member influences the range of motion and resistance response of the forefoot member.

9. The prosthetic foot of claim 1, further comprising:
   a flexible and resilient wedge member disposed between the forefoot member and the forefoot reinforcement member at a location proximal to the attachment.

10. A prosthetic foot comprising:
    a resilient forefoot member having a base end coupled proximal an attachment location and extending forward to a toe end at a toe location, the forefoot member defining an arch section between the base and toe ends, and having a range of motion with multiple stages of advancement including at least a normal range and an extreme range and having a resistance response to an applied force;
    a resilient heel member having a base end coupled to the resilient forefoot member and extending rearward to a heel end at a heel location, the heel member having a range of motion including a normal range and an extreme range and having a resistance response to an applied force; and
    a heel reinforcement member having a base section coupled to the forefoot member at the arch section and extending to a free end proximal to a location between the arch section and the attachment location, the free end being disposed within the extreme range of motion of the forefoot member and moveable with respect to the forefoot member, the heel reinforcement member having a range of motion within the extreme range of motion of the forefoot member, such that the heel reinforcement member influences the range of motion and resistance response of the forefoot member and the heel member.

11. The prosthetic foot of claim 10, wherein the heel reinforcement member forms an arcuate section extending near the heel location and within the extreme range of motion of the heel member.

12. The prosthetic foot of claim 10, further comprising:
a flexible restraint coupled to and between the free end of the heel reinforcement member and the forefoot member, the restraint being flexible in a direction towards the heel reinforcement member to allow the forefoot member to move towards the heel reinforcement member, but substantially non-flexible in a direction away from the heel reinforcement member to couple the forefoot member to the heel reinforcement member in movement away from the heel reinforcement member.

13. The prosthetic foot of claim 10, wherein a flexible cushion is disposed between the free end of the heel reinforcement member and the forefoot member.

14. The prosthetic foot of claim 10, wherein an air bag containing air is disposed between the free end of the heel reinforcement member and the forefoot member.

15. The prosthetic foot of claim 14, wherein the air bag has an opening; and further comprising means for varying the pressure of the air in the air bag coupled to the opening.

16. The prosthetic foot of claim 10, further comprising:
a forefoot reinforcement member having a base section coupled to the forefoot member at the arch section and extending above the forefoot member to a free end proximal the attachment location and spaced from the forefoot member, the free end being disposed within the extreme range of motion of the forefoot member and having a range of motion within the extreme range of motion of the forefoot member, such that the forefoot reinforcement member influences the range of motion and resistance response of the forefoot member.

17. The prosthetic foot of claim 10, further comprising:
a secondary forefoot reinforcement member having a base section coupled to the forefoot member at the arch section and extending to a free end proximal the toe location and spaced above the toe end of the forefoot member, the free end of the secondary forefoot reinforcement member being disposed within the extreme range of motion of the forefoot member and having a range of motion within the extreme range of motion of the forefoot member, such that the secondary forefoot reinforcement member influences the range of motion and resistance response of the forefoot member.

18. The prosthetic foot of claim 10, further comprising:
a flexible and resilient wedge member disposed between the forefoot member and the heel member at a location proximal to the attachment.

19. A prosthetic foot comprising:
a resilient forefoot member having a base end coupled proximal an attachment location and extending forward to a toe end at a toe location, the forefoot member defining an arch section between the base end and the toe end, each of the base end and the toe end having a range of motion with multiple stages of advancement including at least a normal range and an extreme range and having a resistance response to an applied force;
a forefoot reinforcement member having a base section coupled to the forefoot member at the arch section and extending over the forefoot member to a free end at a location between the arch section and the attachment location and spaced from the forefoot member, the free end being disposed within the extreme range of motion of the base end of the forefoot member and having a range of motion within the extreme range of motion of the base end of the forefoot member, such that the forefoot reinforcement member influences the range of motion and resistance response of the base end of the forefoot member; and
a resilient heel member having a base end coupled to the resilient forefoot member and extending rearward to a heel end at a heel location, each of the base end and the heel end having a range of motion including a normal range and an extreme range and having a resistance response to an applied force.

20. The prosthetic foot of claim 19, further comprising:
a heel reinforcement member having a base section coupled to the forefoot member at the arch section and extending under the forefoot member to a free end proximal to a location between the arch section and the attachment location, the free section being disposed within the extreme range of motion of the base end of the forefoot member and moveable with respect to the base end of the forefoot member, the heel reinforcement member having a range of motion within the extreme range of motion of the base end of the forefoot member, such that the heel reinforcement member influences the range of motion and resistance response of the forefoot member.

21. The prosthetic foot of claim 20, wherein the heel reinforcement member forms an arcuate section extending near the heel location and within the extreme range of motion of the heel member.

22. The prosthetic foot of claim 19, further comprising:
a flexible restraint coupled to and between the free end of the forefoot reinforcement member and the forefoot member, the restraint being flexible in a direction towards the forefoot reinforcement member to allow the forefoot member to move towards the forefoot reinforcement member, but substantially non-flexible in a direction away from the forefoot reinforcement member to couple the forefoot member to the forefoot reinforcement member in movement away from the forefoot reinforcement member.

23. The prosthetic foot of claim 19, wherein a flexible cushion is disposed between the free end of the forefoot reinforcement member and the forefoot member.

24. The prosthetic foot of claim 19, further comprising:
a secondary forefoot reinforcement member having a base section coupled to the forefoot member at the arch section and extending to a free end proximal the toe location and spaced above the toe end of the forefoot member, the free end of the secondary forefoot reinforcement member being disposed within the extreme range of motion of the forefoot member and having a range of motion within the extreme range of motion of the forefoot member, such that the secondary forefoot reinforcement member influences the range of motion and resistance response of the forefoot member.

25. The prosthetic foot of claim 19, further comprising:
a flexible and resilient wedge member disposed between the forefoot member and the heel member at a location proximal to the attachment between the forefoot member and the heel member.

26. The prosthetic foot of claim 19, further comprising:
a flexible and resilient wedge member disposed between the forefoot member and the forefoot reinforcement member at a location proximal to the attachment between the forefoot member and the forefoot reinforcement member.

27. The prosthetic foot of claim 1, further comprising:

a resilient heel member having a base end coupled to the resilient forefoot member and extending rearward to a heel end at a heel location, the heel member having a range of motion including a normal range and an extreme range and having a resistance response to an applied force; and wherein both the forefoot reinforcement member and the resilient heel member are coupled to the forefoot member at substantially the same location at the arch section.

* * * * *